(12) United States Patent
Hendricks et al.

(10) Patent No.: US 10,800,931 B2
(45) Date of Patent: Oct. 13, 2020

(54) CONDUCTIVE POLYMERIC COATINGS, MEDICAL DEVICES, COATING SOLUTIONS AND METHODS

(71) Applicant: Heraeus Medical Components LLC, St. Paul, MN (US)

(72) Inventors: Jeffrey L. Hendricks, Ann Arbor, MI (US); Sarah M. Richardson-Burns, Ann Arbor, MI (US); Kyle Mallires, Ann Arbor, MI (US); Sarah A. Spanninga, Ann Arbor, MI (US); Nathan A. Lockwood, Minneapolis, MN (US); Robert W. Hergenrother, Eden Prairie, MN (US); Bruce M. Jelle, Chanhassen, MN (US)

(73) Assignee: Heraeus Medical Components LLC, St. Paul, MN (US)

( * ) Notice: Subject to any disclaimer, the term of this patent is extended or adjusted under 35 U.S.C. 154(b) by 478 days.

(21) Appl. No.: 14/914,586

(22) PCT Filed: Aug. 25, 2014

(86) PCT No.: PCT/US2014/052542
§ 371 (c)(1),
(2) Date: Feb. 25, 2016

(87) PCT Pub. No.: WO2015/031265
PCT Pub. Date: Mar. 5, 2015

(65) Prior Publication Data
US 2016/0208114 A1    Jul. 21, 2016

Related U.S. Application Data

(60) Provisional application No. 61/869,749, filed on Aug. 25, 2013.

(51) Int. Cl.
*A61B 5/04* (2006.01)
*A61N 1/04* (2006.01)
(Continued)

(52) U.S. Cl.
CPC .............. *C09D 5/24* (2013.01); *A61B 5/6846* (2013.01); *A61N 1/05* (2013.01); *C09D 5/4476* (2013.01);
(Continued)

(58) Field of Classification Search
CPC ............ A61B 5/0408; A61B 2562/125; A61B 5/04087; A61B 5/6833; A61B 2562/046;
(Continued)

(56) References Cited

U.S. PATENT DOCUMENTS 4,674,512 A * 6/1987 Rolf ..................... H01B 1/20
600/391
4,979,959 A    12/1990 Guire
(Continued)

FOREIGN PATENT DOCUMENTS

WO    2013/109930 A1    7/2013

OTHER PUBLICATIONS

Sotzing et al. "Poly(3,4-ethylenedioxythiophene) (PEDOT) Prepared via Electrochemical Polymerization of EDOT, 2,2'-Bis(3,4-ethylenedioxythiophene) (BiEDOT), and Their TMS Derivatives" Advanced Materials 9. No. 10. 1997.*
(Continued)

*Primary Examiner* — Eun Hwa Kim
*Assistant Examiner* — Brian M Antiskay
(74) *Attorney, Agent, or Firm* — Stradley Ronon Stevens & Young, LLP

(57) ABSTRACT

The invention includes conductive polymeric coatings, medical device, coating solutions and methods of making the same. A coating solution for forming a conductive
(Continued)

polymer layer can include a conductive monomer, at least one photoreactive component comprising an anionic photoreactive cross-linking agent or an anionic photoreactive hydrophilic polymer, and a solvent. A medical device can include an electrode and an electrically conductive coating disposed over the electrode. The electrically conductive coating can include a reaction product of the conductive monomer and the at least one photoreactive component. Other aspects are included herein.

11 Claims, 2 Drawing Sheets

(51) Int. Cl.
    *C09D 5/24*     (2006.01)
    *C09D 5/44*     (2006.01)
    *A61N 1/05*     (2006.01)
    *A61B 5/00*     (2006.01)
    *A61B 18/12*     (2006.01)
    *A61B 18/00*     (2006.01)

(52) U.S. Cl.
    CPC ..... *A61B 18/12* (2013.01); *A61B 2018/00071* (2013.01); *A61B 2018/00136* (2013.01)

(58) Field of Classification Search
    CPC . A61B 5/08; A61B 5/6832; A61B 2562/0217; A61B 2017/00831; A61L 27/52; A61N 1/0492; Y10T 428/12479
    USPC .......................... 600/372, 382–395; 252/500
    See application file for complete search history.

(56) References Cited

U.S. PATENT DOCUMENTS

| | | | |
|---|---|---|---|
| 4,981,729 A * | 1/1991 | Zaleski | B05D 7/02 252/500 |
| 5,002,582 A | 3/1991 | Guire et al. | |
| 5,263,992 A | 11/1993 | Guire | |
| 5,512,329 A | 4/1996 | Guire et al. | |
| 5,637,460 A | 6/1997 | Swan et al. | |
| 5,714,360 A | 2/1998 | Swan et al. | |
| 6,254,634 B1 * | 7/2001 | Anderson | A61L 27/34 427/489 |
| 6,278,018 B1 | 8/2001 | Swan | |
| 6,391,937 B1 * | 5/2002 | Beuhler | C08F 8/00 428/474.4 |
| 8,343,212 B2 | 1/2013 | Pickett et al. | |
| 8,586,702 B2 * | 11/2013 | Martin | C07D 495/04 528/30 |
| 2005/0060015 A1 | 3/2005 | Tanaka | |
| 2010/0048815 A1 * | 2/2010 | Ying | C08G 61/123 525/54.2 |
| 2011/0021899 A1 * | 1/2011 | Arps | A61K 9/0009 600/372 |
| 2011/0087315 A1 | 4/2011 | Richardson-Burns et al. | |
| 2011/0135923 A1 * | 6/2011 | Ahn | C09J 133/08 428/355 AC |
| 2012/0046384 A2 | 2/2012 | Kurdyumov et al. | |
| 2012/0100217 A1 | 4/2012 | Green et al. | |

OTHER PUBLICATIONS

Nilasaroya, A., et al., "Structural and Functional Characterisation of Poly(vinyl alcohol) and Heparin Hydrogels," Biomaterials, 2008, pp. 4658-4664, vol. 29, No. 35.

* cited by examiner

CONDUCTIVE POLYMERIC COATINGS, MEDICAL DEVICES, COATING SOLUTIONS AND METHODS

This application is being filed as a PCT International Patent application on Aug. 25, 2014 in the name of SurModics, Inc., a U.S. national corporation, applicant for the designation of all countries and Jeffrey L. Hendricks, a U.S. citizen, Sarah M. Richardson-Burns, a U.S. citizen, Kyle Mallires, a U.S. citizen, and Sarah A. Spanninga, a U.S. citizen, inventors and applicants for the designation of all countries, and Nathan A. Lockwood, a U.S. citizen, Robert W. Hergenrother, a U.S. citizen, and Bruce M. Jelle, a U.S. citizen, inventors only for the designation of all countries, and claims priority to U.S. Provisional Patent Application No. 61/869,749, filed Aug. 25, 2013, the contents of which are herein incorporated by reference in its entirety.

FIELD OF THE INVENTION

The present invention relates to conductive polymeric coatings, medical devices, coating solutions and methods of making the same.

BACKGROUND

While many polymers are strong electrical resistors, it will be appreciated that there are also various electrically conducting polymers. Such polymers have many applications in electronics, medical technologies and general industrial settings. By way of example, various conductive polymers have been applied as coatings over substrates, such as over electrodes on medical devices.

SUMMARY

Aspects herein include conductive polymeric coatings, coating solutions (i.e., polymerization mixtures) for forming such coatings, and methods of making the same.

Coating solutions for forming a conductive polymer layer are provided. The coating solution can include a conductive monomer, at least one photoreactive component, the photoreactive component comprising an anionic photoreactive cross-linking agent or an anionic photoreactive hydrophilic polymer, and a solvent.

Electrically conductive coatings are provided. The electrically conductive coating can include a reaction product of a polymerization mixture comprising a conductive monomer and at least one photoreactive component, the photoreactive component comprising an anionic photoreactive cross-linking agent or an anionic photoreactive hydrophilic polymer.

Coated electrodes are provided. The coated electrode can include an electrode and an electrically conductive coating disposed over the electrode. The electrically conductive coating can include a reaction product of a polymerization mixture comprising a conductive monomer and at least one photoreactive component, the photoreactive component comprising an anionic photoreactive cross-linking agent or an anionic photoreactive hydrophilic polymer.

Medical devices are provided. The medical device can include a coated electrode. The coated electrode can include an electrode and an electrically conductive coating disposed over the electrode. The electrically conductive coating can include a reaction product of a polymerization mixture comprising a conductive monomer and at least one photoreactive component, the photoreactive component comprising an anionic photoreactive cross-linking agent or an anionic photoreactive hydrophilic polymer.

Methods for electrodepositing a coating onto a surface of a substrate are provided. The method can include contacting the surface of the substrate with a coating solution. The coating solution can include a conductive monomer, at least one photoreactive component, the photoreactive component comprising an anionic photoreactive cross-linking agent or an anionic photoreactive hydrophilic polymer, and a solvent. The method can further include applying an electrical potential to the surface of the substrate and the coating solution sufficient to polymerize the conductive monomer.

The application of an electrical potential to the surface of the substrate can provide a mechanically durable coating onto the surface of the substrate that resists delamination. The application of an electrical potential to the surface of the substrate can provide an electrically durable coating onto the surface of the substrate.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope of the present invention is defined by the appended claims and their legal equivalents.

BRIEF DESCRIPTION OF THE FIGURES

Aspects may be more completely understood in connection with the following drawings, in which.

Figure 1:
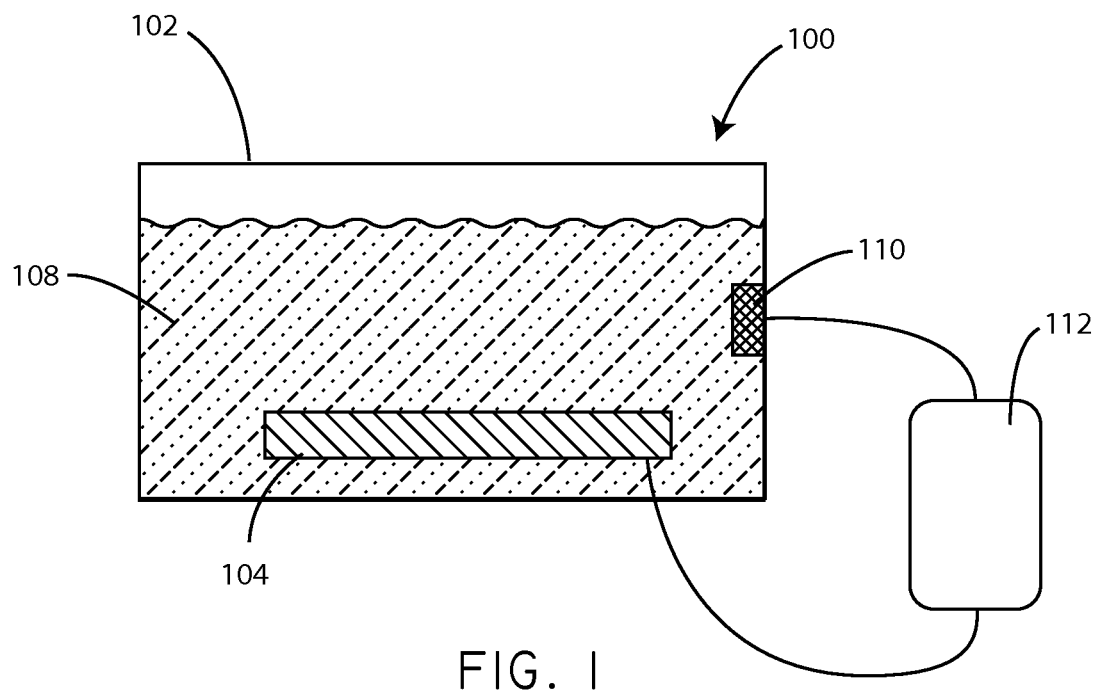
FIG. 1 is a schematic diagram of a system for coating a substrate in accordance with aspects herein.

While the invention is susceptible to various modifications and alternative forms, specifics thereof have been shown by way of example and drawings, and will be described in detail. It should be understood, however, that the invention is not limited to the particular embodiments described. On the contrary, the intention is to cover modifications, equivalents, and alternatives falling within the spirit and scope of the invention.

DETAILED DESCRIPTION

The embodiments of the present invention described herein are not intended to be exhaustive or to limit the invention to the precise forms disclosed in the following detailed description. Rather, the embodiments are chosen and described so that others skilled in the art can appreciate and understand the principles and practices of the present invention.

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

As described above, electrically conducting polymers have many applications in electronics, medical technologies and general industrial settings. As one example, relevant to medical technologies, electrically conducting polymers have been applied over portions of medical devices such as over electrodes, sensors, cases, or the like.

However, it has been observed that electrically conducting polymers when applied as coatings may exhibit durability that is less than desirable for some applications. For example, it has been observed that coatings made of electrochemically deposited PEDOT with polystyrene sulfonate (PSS) as the counterion can be mechanically stiff, brittle, and prone to cracking and delamination when stressed.

Electrically conductive polymeric coatings included herein can exhibit improved properties such as enhanced durability and resistance to delamination.

Coating solutions herein can include a conductive monomer, at least one photoreactive component comprising an anionic photoreactive cross-linking agent or an anionic photoreactive hydrophilic polymer, and a solvent to provide a conductive polymeric coating on at least a portion of the surface of a substrate.

In addition medical devices, for example medical devices including electrodes, coated in accordance with aspects herein can exhibit improved electrical properties in comparison with bare metal medical devices. For example, the polymeric coatings described herein can provide a metal medical device electrode with (a) 1 to 3 orders of magnitude decrease in electrode impedance, (b) an increase in charge storage capacity (CSC) often as high as approximately 1000%, and/or (c) significantly reduced electrode polarization or peak to peak voltage/current response to a biphasic current or voltage pulse.

The polymeric coatings described herein can be used to produce medical electrodes having excellent electrical and tissue-interfacing properties that enable better sensing and/or stimulation performance for short-term and long-term medical device applications, as compared to uncoated electrodes or electrodes coated with existing, state of the art coatings.

The coatings can be deposited on a substrate surface. The substrate and/or substrate surface can include various materials, examples of which include an electrically conductive material, such as metals, ceramics, polymers, composites, and the like.

The substrate surface can include a carbon nitride, a carbon cloth, a carbon paper, a carbon screen printed electrode, a carbon black, a carbon powder, a carbon fiber, a carbon nanotube, a diamond-coated conductor, a glassy carbon, a mesoporous carbon, a graphite, or a combination thereof.

The substrate surface can include a non-metallic inorganic material. For example, the non-metallic inorganic material can include a metal oxide, a metal nitride, a ceramic, a metalloid, or a combination thereof. The non-metallic inorganic material can include, for example, a metalloid selected from the group consisting of silicon, carbon, and a combination thereof.

The substrate surface can include a metal oxide. For example, the metal oxide can include aluminum, titanium, zirconium, hafnium, tantalum, molybdenum, chromium, nickel, tungsten, rhenium, iridium, or a combination thereof.

The substrate surface can include a ceramic. For example, the ceramic can include a silicon nitride, titanium nitride, a silicon carbide, a silicon oxide, a calcium phosphate, an indium-tin oxide, or a combination thereof.

The substrate surface can include a metal selected from the group consisting of a noble metal, a transition metal, or a combination thereof. For example, the metal can be selected from the group consisting of gold, platinum, palladium, iridium, osmium, rhodium, titanium, tantalum, tungsten, ruthenium, magnesium, iron, and a combination thereof.

The substrate surface can include a non-noble metal. For example, the non-noble metal can be selected from the group consisting of titanium, tantalum, and a combination thereof.

The substrate surface can include a metal alloy. For example, the metal alloy includes at least one noble metal and at least one transition metal. By way of non-limiting example, the metal alloy can include iron, sulfur, manganese, and molybdenum; iron and chromium; nickel and titanium; nickel and cobalt; cobalt and chromium; cobalt, chromium and iron; cobalt, chromium and nickel; cobalt, chromium, nickel and tungsten; nickel and chromium; magnesium and iron; or a combination thereof. For example, the metal alloy can include nickel and cobalt. The metal alloy can also be a stainless steel alloy selected from the group consisting of stainless steel 304L, stainless steel 316L, stainless steel 316LVM, and a combination thereof. The metal alloy can also be a cobalt-nickel-chrome alloy selected from the group consisting of MP35N, 35NLT, and a combination thereof. The metal alloy can also include the titanium alloy Ti-6Al 4V. The metal alloy can include Nitinol.

Generally, the substrate itself can have almost any form, including but not limited to metal pieces, coupons, meshes, wires, blocks, tubes, and/or spheres. The conductive substrate can include all or part of one or more electrodes on a device, for example a medical device.

The electrically conductive substrate is coated with a polymeric coating of suitable thickness, such as from about 25 nm to about 10 μm, or from about 200 nm to about 10 μm, or from about 500 nm to about 5 μm.

Coatings can be formed using the coating solutions. The coating solutions can include various components including, but not limited to monomers, anionic photoreactive cross-linking agents, anionic photoreactive hydrophilic polymers, non-charged photoreactive hydrophilic polymers, solvents, and surfactants. It will be appreciated that the coating solutions can include less than all of the above components, or can include components in addition to those above. Aspects of these components will now be described in greater detail.

The monomer can include one or more distinct monomers. The monomer(s) can include those that polymerize to form an electrically conductive polymer. The monomer(s) can specifically include conductive monomers. The term "conductive monomer" as used herein shall refer to monomers that polymerize to form an electrically conductive polymer.

The conductive monomer can include acetylene, fluorene, para-phenylene, pyrene, pyrrole, carbazole, indole, phenyl azide, aniline, thiophene, pyridine, or a mixture or functionalized derivative thereof.

The conductive monomer can comprise 3,4-ethylenedioxythiophene or a functionalized derivative, dimerized derivative or trimerized derivative thereof. For example, the conductive monomer can comprise 3,4-ethylenedioxythiophene (EDOT), hydroxymethyl-EDOT, EDOT-vinyl, EDOT-ether allyl, EDOT-COOH, EDOT-MeOH, EDOT-silane, EDOT-vinyl, EDOT-acrylate, EDOT-sulfonate, EDOT-amine, EDOT-amide, bi-EDOT, tri-EDOT or a combination thereof.

The functionalized derivative of EDOT is preferably selected from the group consisting of hydroxymethyl-EDOT, EDOT-vinyl, EDOT-ether allyl, EDOT-acrylate, and combinations thereof.

The functionalized derivative of EDOT can comprise an alkene functional group.

The conductive monomer can include a mixture of EDOT and a functionalized EDOT derivative. The molar ratio of EDOT to the functionalized EDOT derivative is preferably from about 0.5:1 to about 10:1, and more preferably, from about 0.5:1 to about 2:1.

The conductive monomer can include a propylenedioxythiophene such as ProDOT (3,4-propylenedioxythiophene), 3,4-(2,2-dimethylpropylenedioxy)thiophene, 3,4-(2',2'-diethylpropylene)dioxythiophene, or a functionalized derivative, dimerized derivative or trimerized derivative thereof. For example, the conductive monomer can comprise ProDOT, hydroxymethyl-ProDOT, ProDOT-vinyl, ProDOT-ether allyl, ProDOT-COOH, ProDOT-MeOH, ProDOT-silane, ProDOT-silanol, ProDOT-vinyl, ProDOT-acrylate, ProDOT-sulfonate, ProDOT-amine, ProDOT-amide, bi-ProDOT, tri-ProDOT or a combination thereof.

The conductive monomer can include hexylthiophene or a functionalized derivative thereof, 4-vinylpyridine, or 3-methyl thiophene.

The amount of the monomer used in the solution can vary. For example, the amount of monomer can be from about 0.001M to about 1M. As another example, the amount of monomer can be from about 0.01M to about 0.2M, such as about 0.09M.

Electrically conductive polymers formed from the monomer can include multiple conducting repeat units assembled into chains with conjugated alternating single and double carbon-carbon bonds. Conductive polymers are also sometimes referred to as inherently or intrinsically conducting polymers, electroactive polymers, or conjugated polymers. Conductive polymers are ideally suited for joining or interfacing electronic and ionic systems, because they are capable of conducting both electronic and ionic charge. Conductive polymers can also utilize highly effective and efficient charge storage and transfer mechanisms, similar to capacitors.

The conductive monomer or the conductive polymer can be cationic. For example, when the polymerization mixture includes a conductive polymer, the conductive polymer can carry an average charge per repeat unit of from about +0.1 to about +1.0, or from about +0.25 to about +0.5. Preferably, the conductive polymer carries an average charge per repeat unit of about +0.33.

The conductive polymer can include a polyacetylene, a poly(vinyl alcohol), a poly(fluorene), a polyphenylene, a polyphenylene vinylene, a polypyrene, a polyazulene, a polynaphthalene, a poly(pyrrole), a polycarbazole, a polyindole, a polyazepine, a polyaniline, a polyacene, a polythiophene, a polythiophene vinylene, a poly(p-phenylene sulfide), a polypyridine, or functionalized derivatives, precursors or blends thereof.

The conductive polymer can comprise poly(3,4-ethylenedioxythiophene), or a functionalized derivative thereof. For example, the conductive polymer can be derived from 3,4-ethylenedioxythiophene.

The conductive polymer can be derived from a functionalized derivative of EDOT selected from the group consisting of hydroxymethyl-EDOT, EDOT-vinyl, EDOT-ether allyl, EDOT-COOH, EDOT-MeOH, EDOT-silane, EDOT-vinyl, EDOT-acrylate, EDOT-sulfonate, EDOT-amine, EDOT-amide, and combinations thereof. As an example, the functionalized derivative of 3,4-ethylenedioxythiophene (EDOT) can be selected from the group consisting of hydroxymethyl-EDOT, EDOT-vinyl, EDOT-ether allyl, EDOT-acrylate, and combinations thereof.

Conductive polymers having allyl-terminated pendent groups as described in U.S. Pat. No. 8,343,212 (Pickett et al.), which is incorporated herein by reference, can also be used as the conductive polymer.

The conductive polymer can be derived from a propylenedioxythiophene such as ProDOT (3,4-propylenedioxythiophene), 3,4-(2,2-dimethylpropylenedioxy)thiophene, 3,4-(2',2'-diethylpropylene)dioxythiophene, or a functionalized derivative thereof. For example, the conductive polymer can comprise poly(3,4-propylenedioxythiophene), poly(3,4-(2,2-dimethylpropylenedioxy)thiophene), or poly(3,4-(2',2'-diethylpropylene)dioxythiophene).

The conductive polymer can include poly(hexylthiophene), or a salt or functionalized derivative thereof. The conductive polymer can include poly-4-vinylpyridine. The conductive polymer can include poly(diallyldimethylammonium chloride).

The coating solution can also include an anionic photoreactive cross-linking agent. The cross-linking agents can include those with at least two photoreactive groups.

The photoactivatable cross-linking agent can be anionic, and can have good solubility in an aqueous composition.

When at least one anionic photoactivatable cross-linking agent is used to form the coating, the cross-linking agent can crosslink other components within the coating layer which can also improve the durability of the coating.

Various anionic photoactivatable cross-linking agents can be used. For example, the anionic photoactivatable cross-linking agent can comprise a compound of formula I: $X_1$—Y—$X_2$ where Y is a radical containing at least one acidic group or a salt of an acidic group; and $X_1$ and $X_2$ are each independently a radical containing a latent photoreactive group. The photoreactive groups can be one or more of those described herein, such as an aryl ketone or a quinone. Spacers can also be part of $X_1$ or $X_2$ along with the latent photoreactive group.

The radical Y in formula I provides the desired water solubility for the anionic photoactivatable cross-linking agent. The water solubility (at room temperature and optimal pH) is at least about 0.05 mg/ml. For example, the solubility is about 0.1 to about 10 mg/ml or about 1 to about 5 mg/ml.

In the compound of formula I, Y can be a radical containing at least one acidic group or salt thereof. Such a photoactivatable cross-linking agent can be anionic depending upon the pH of the coating composition. Suitable acidic groups include, for example, sulfonic acids, carboxylic acids, phosphonic acids, and the like. Suitable salts of such groups include, for example, sulfonate, carboxylate, and phosphate salts. As an example, the cross-linking agent can include a sulfonic acid or sulfonate group. Suitable counter ions include alkali, alkaline earths metals, ammonium, protonated amines, and the like.

For example, a compound of formula I can have a radical Y that contains a sulfonic acid or sulfonate group; $X_1$ and $X_2$ can contain photoreactive groups such as aryl ketones. Such compounds include 4,5-bis(4-benzoylphenylmethyleneoxy)benzene-1,3-disulfonic acid or a salt thereof; 2,5-bis(4-benzoylphenylmethyleneoxy)benzene-1,4-disulfonic acid or a salt thereof; 2,5-bis(4-benzoylmethyleneoxy)benzene-1-sulfonic acid or a salt thereof; N,N-bis[2-(4-benzoylbenzyloxy)ethyl]-2-aminoethanesulfonic acid or a salt thereof; bis(4-benzoylphenyl) phosphoric acid or a salt thereof; and the like. See U.S. Pat. No. 6,278,018, and U.S. Publ. App. No. 2012/0046384 for such compounds of formula I. The counter ion of the salt can be, for example, ammonium or an alkali metal such as sodium, potassium, or lithium. For example, the anionic photoreactive cross-linking agents can be selected from the group consisting of disodium 4,5-bis [(4-benzoylbenzyl)oxy]-1,3-benzenedisulfonate (DBDS) and sodium bis(4-benzoylphenyl) phosphate.

The coating solution can include at least about 0.5 mg/ml of the anionic photoreactive cross-linking agent, such as from about 0.5 mg/ml to about 25 mg/ml of the anionic photoreactive cross-linking agent. For example, the solution can include from about 5 mg/ml to about 15 mg/ml of the anionic photoreactive cross-linking agent.

The coating solution can include an anionic photoreactive hydrophilic polymer. Hydrophilic polymers can include those that are anionic. Anionic hydrophilic polymers can specifically include homopolymers, copolymers, terpolymers, and the like.

When at least one anionic hydrophilic polymer is used to form the coating, the anionic hydrophilic polymer can be derivatized with photoreactive groups. The photoreactive groups can be the same as those described herein.

The anionic hydrophilic polymer can include polymers including polyacrylamide and photoreactive groups ("Photo-PA"). The anionic hydrophilic polymer can include polyacrylamide and can include sulfonate groups. For example, the anionic hydrophilic polymer can include acrylamido-2-methylpropanesulfonate groups (AMPS) and polyethylene glycol segments.

The polymer comprising polyacrylamide can be selected from the group consisting of N-acetylated poly[acrylamide-co-sodium-2-acrylamido-2-methylpropanesulfonate-co-N-(3-(4-benzoylbenzamido)propyl)methacrylamide]-co-methoxy poly(ethylene glycol) and poly[acrylamide-co-sodium-2-acrylamido-2-methylpropanesulfonate-co-N-(3-(4-benzoylbenzamido)propyl)methacrylamide]. Additional polymers comprising polyacrylamide are described in U.S. Pat. Nos. 4,979,959; 5,263,992; and 5,512,329, the disclosure of which is herein incorporated by reference in its entirety.

The coating solution can include at least about 0.5 mg/ml of the anionic hydrophilic polymer. For example, the solution can include at least about 2.5 mg/ml of the anionic hydrophilic polymer. As another example, the solution can include from about 2.5 mg/ml to about 50 mg/ml of the anionic hydrophilic polymer. As another example, the solution can include from about 5 mg/ml to about 50 mg/ml of the anionic hydrophilic polymer, or from about 2.5 mg/ml to about 25 mg/ml of the anionic hydrophilic polymer.

As used herein, the phrases "latent photoreactive group" and "photoreactive group" are used interchangeably and refer to a chemical moiety that is sufficiently stable to remain in an inactive state (i.e., ground state) under normal storage conditions but that can undergo a transformation from the inactive state to an activated state when subjected to an appropriate energy source. Unless otherwise stated, references to photoreactive groups herein shall also include the reaction products of the photoreactive groups. Photoreactive groups respond to specific applied external stimuli to undergo active specie generation with resultant covalent bonding to an adjacent chemical structure. For example, a photoreactive group can be activated and can abstract a hydrogen atom from an alkyl group. A covalent bond can then form between the compound with the photoreactive group and the compound with the C—H bond. Suitable photoreactive groups are described in U.S. Pat. No. 5,002,582, the disclosure of which is incorporated herein by reference.

Photoreactive groups can be chosen to be responsive to various portions of actinic radiation. For example, groups can be chosen that can be photoactivated using either ultraviolet or visible radiation. Suitable photoreactive groups include, for example, azides, diazos, diazirines, ketones, and quinones. The photoreactive groups generate active species such as free radicals including, for example, nitrenes, carbenes, and excited states of ketones upon absorption of electromagnetic energy.

The photoreactive group can comprise an aryl ketone, such as acetophenone, benzophenone, anthrone, and anthrone-like heterocycles (i. e., heterocyclic analogs of anthrone such as those having N, O, or S in the 10-position), or their substituted (e.g., ring substituted) derivatives. Examples of aryl ketones include heterocyclic derivatives of anthrone, including acridone, xanthone, and thioxanthone, and their ring substituted derivatives. Other suitable photoreactive groups include quinone such as, for example anthraquinone.

The functional groups of such aryl ketones can undergo multiple activation/inactivation/reactivation cycles. For example, benzophenone is capable of photochemical excitation with the initial formation of an excited singlet state that undergoes intersystem crossing to the triplet state. The excited triplet state can insert into carbon-hydrogen bonds by abstraction of a hydrogen atom (from a polymeric coating layer, for example), thus creating a radical pair. Subsequent collapse of the radical pair leads to formation of a new carbon-carbon bond. If a reactive bond (e.g., carbon/hydrogen) is not available for bonding, the ultraviolet light-induced excitation of the benzophenone group is reversible and the molecule returns to ground state energy level upon removal of the energy source. Photoreactive aryl ketones such as benzophenone and acetophenone can undergo multiple reactivations in water and hence can provide increased coating efficiency.

The azides constitute another class of photoreactive groups and include arylazides ($C_6R_5N_3$) such as phenyl azide and 4-fluoro-3-nitrophenyl azide; acyl azides (—CO—$N_3$) such as benzoyl azide and p-methylbenzoyl azide; azido formates (—O—CO—$N_3$) such as ethyl azidoformate and phenyl azidoformate; sulfonyl azides (—$SO_2$—$N_3$) such as benzenesulfonyl azide; and phosphoryl azides $(RO)_2PON_3$ such as diphenyl phosphoryl azide and diethyl phosphoryl azide.

Diazo compounds constitute another class of photoreactive groups and include diazoalkanes (—$CHN_2$) such as diazomethane and diphenyldiazomethane; diazoketones (—CO—$CHN_2$) such as diazoacetophenone and 1-trifluoromethyl-1-diazo-2-pentanone; diazoacetates (—O—CO—$CHN_2$) such as t-butyl diazoacetate and phenyl diazoacetate; and beta-keto-alpha-diazoacetates (—CO—$CN_2$—CO—O—) such as t-butyl alpha diazoacetoacetate.

Other photoreactive groups include the diazirines (—$CHN_2$) such as 3-trifluoromethyl-3-phenyldiazirine; and ketenes (—CH=C=O) such as ketene and diphenylketene.

In some aspects, the photoreactive groups can be aryl ketones, such as benzophenone.

It will be appreciated that various other components can be included within coatings solutions as described herein. Additional polymers can be included, such as one or more non-charged photoreactive hydrophilic polymers. The non-charged photoreactive hydrophilic polymer can be a homopolymer, copolymer, or terpolymer. The photoreactive hydrophilic polymer can include subunits of polymerized 1-vinyl-2-pyrrolidone (PVP) and can include photoreactive functional groups such as those described herein ("Photo-PVP"). For example, the hydrophilic polymer can include subunits of polymerized N-(3-aminopropyl)methacrylamide, wherein at least some are photoderivatized. An exemplary non-charged photoreactive hydrophilic polymer can be prepared by a copolymerization of 1-vinyl-2-pyrrolidone and N-(3-aminopropyl)methacrylamide (APMA), followed by photoderivatization of the polymer using 4-benzoylbenzoyl chloride under Schotten-Baumann conditions. The unreacted amines of the photopolymer can further be acetylated using acetic anhydride to give acetylated photo-PVP. Exemplary non-charged photoreactive hydrophilic polymers include those described in U.S. Pat. No. 5,714,360, the disclosure of which is herein incorporated by reference.

The solution can include at least about 0.5 mg/ml of the non-charged photoreactive hydrophilic polymer. As an example, the solution can include at least about 2.5 mg/ml of the non-charged photoreactive hydrophilic polymer. As another example, the solution can include from about 2.5 mg/ml to about 50 mg/ml of the non-charged photoreactive hydrophilic polymer. As another example, the solution can include from about 5 mg/ml to about 50 mg/ml of the non-charged photoreactive hydrophilic polymer, or from about 2.5 mg/ml to about 25 mg/ml of the non-charged photoreactive hydrophilic polymer.

The solution can include both an anionic hydrophilic polymer and a non-charged photoreactive hydrophilic polymer. For example, the solution can include an anionic hydrophilic polymer and a non-charged photoreactive hydrophilic polymer in a weight ratio of 1:10 to 10:1. As another example, the solution can include an anionic hydrophilic polymer and a non-charged photoreactive hydrophilic polymer in a weight ratio of 1:2 to 2:1, 1:1.5 to 1.5:1, or about 1:1.

Additional counter ions can be included within the coating solutions and/or coatings. Additional counter ions can include, but are not limited to, alkali metals and alkaline earth metals (including, but not limited to, magnesium, calcium, beryllium, and strontium).

The coating solution can also include a surfactant. Various surfactants can be used. The surfactant component can include one or more nonionic, cationic, anionic, zwitterionic, or amphoteric surfactants, or a combination thereof. For example, the surfactant component can include a nonionic surfactant.

The surfactant can be selected from the group consisting of polaxamers, polyoxyethylene oleyl ethers, polysorbitan, and polyoxyethylene derivatives of sorbitan monolaurate. For example, the surfactant can include a polyoxypropylene-polyoxyethylene polaxamer (sold under the trade name PLURONIC F-68). The surfactant can include a polyoxyethylene glycol alkyl ether, such as polyethylene glycol octadecyl ether (sold under the trade name BRIJ 78). The surfactant can include a polyoxyethylene derivative of sorbitan monolaurate, such as polyoxyethylene (60 or 80) sorbitan monolaurate (sold under the trade names TWEEN 60 and TWEEN 80).

The coating solution can also include one or more solvents, such as water or an organic solvent.

Exemplary organic solvents can include polar organic solvents. For example, the organic solvent can be an aprotic organic solvent. By way of non-limiting example, the aprotic organic solvent can be selected from the group consisting of acetonitrile, dichloromethane, dimethylsulfoxide, acetone, dimethylformamide, and a combination thereof.

The solvent component can include a polar protic solvent. By way of non-limiting example, the polar protic solvent can be selected from the group consisting of water, isopropanol, methanol, ethanol, and a combination thereof.

The solvent can include a mixture of water and one or more organic solvents, such as a mixture of water and one or more aprotic organic solvents (e.g., water and acetonitrile, or water and isopropanol).

Where the solvent component includes water and an aprotic organic solvent, the volumetric ratio of water to the aprotic organic solvent can be from about 1:10 to about 10:1. As an example, the volumetric ratio of water to the aprotic organic solvent can be from about 1:3 to about 3:1.

Methods herein can include methods of depositing conductive polymeric coatings on a surface. The method can include exposing the coating solution to an electrical potential, wherein the solution is in contact with a surface of a substrate which serves as an electrode in the application of the electrical potential. Processes used for electrodeposition can include, but are not limited to, potentiostatic, potentiodynamic, galvanostatic, and galvanodynamic processes.

Referring now to FIG. 1 a schematic diagram of a system 100 for coating a substrate is shown. The system 100 includes a container 102 into which components of the system can be placed. A solution 108 is in contact with the substrate 104. The system 100 also includes an electrode 110 for applying the electric potential (counter or return electrode). The substrate 104 itself can serve as another electrode (working or sense electrode). The system 100 can also include a controller 112 for applying the electric potential as described herein. The controller 112, for example, can be a potentiostat/galvanostat.

Figure 2:
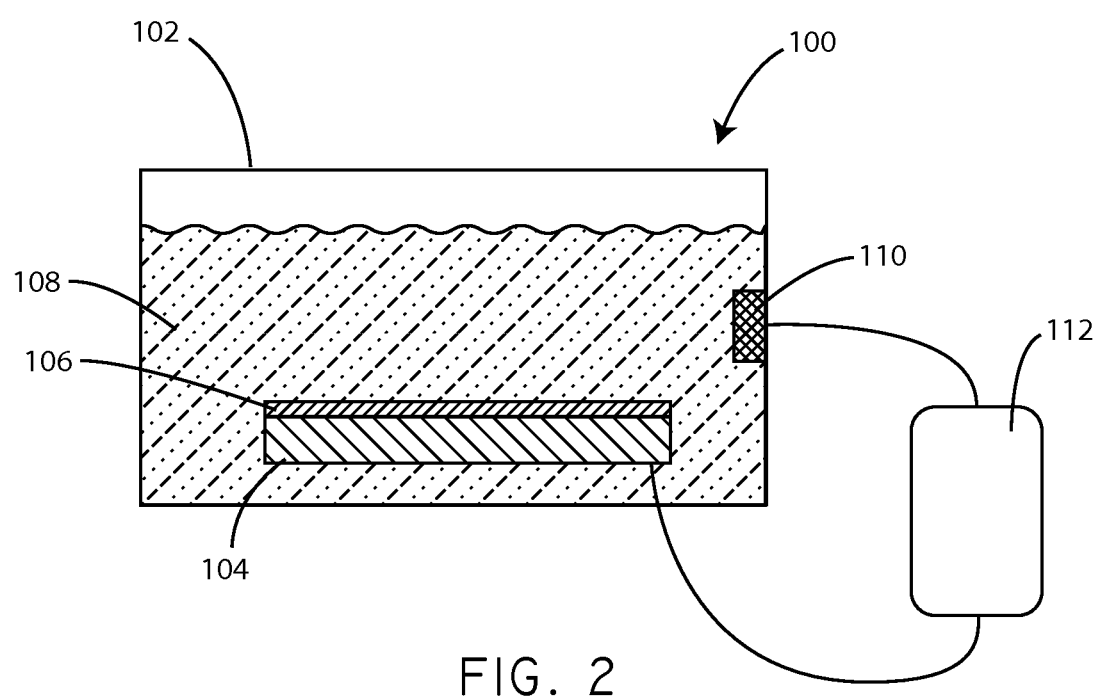
FIG. 2 is a schematic diagram of a system for coating a substrate in accordance with aspects herein.

Referring now to FIG. 2, the system is shown after deposition of a conductive polymeric layer has occurred. In this view, the substrate 104 is shown with a conductive polymeric layer 106 disposed thereon.

Methods of applying coatings herein can include preparing a coating mixture (or polymerization mixture) including components as described herein and electrochemically polymerizing the polymerization mixture to form a polymeric coating in situ on an electrically conductive substrate.

Conductive polymers can be polymerized from their constituent monomers by oxidation reactions driven by electrochemical synthesis at an anode in a liquid electrolyte, or alternatively by chemical synthesis in the presence of an oxidant in liquid or gas. Conducting polymers are commonly manifest as thin films or coatings on conductive or non-conductive substrates and as micro/nanoparticles on a substrate/or surface, or as a dispersion or colloidal suspension in an aqueous or organic solvent.

The electrochemical polymerization reaction can be carried out by first immersing the conductive substrate in the polymerization mixture. When electrical charge is then delivered to the conductive substrate, polymerization is initiated and a polymeric coating is electrodeposited in situ onto the conductive portions of the substrate that are immersed in the polymerization mixture.

It will be appreciated that the various components of the polymerization mixture can be mixed in various orders. For example, a conducting polymer precursor solution including (a) the conductive polymer or conductive monomer and (b) the solvent component is prepared separately from the other components of the polymerization mixture. The concentration of the conductive polymer or conductive monomer in the precursor solution can be from about 0.001M to about 1M. As an example, the concentration can be from about 0.01M to about 0.2M, such as about 0.09M.

To improve the stability of the precursor solution, a surfactant can be added. The conducting polymer precursor solution can be vortexed, agitated, or stirred.

A solution including the anionic photoreactive cross-linking agent and/or anionic photoreactive hydrophilic polymer component(s) can be prepared separately from the conducting polymer precursor solution. The solution comprising the anionic photoreactive cross-linking agent and/or anionic photoreactive hydrophilic polymer component(s) can be combined with the conducting polymer precursor solution to form a polymerization mixture or coating solution.

The coating solution can also undergo one or more preprocessing steps prior to the electrochemical polymerization. For example, the coating solution can be vortexed, agitated, or stirred prior to the electrochemical polymerization step.

The temperature of the coating can be maintained at from about 20° C. to about 40° C. prior to the electrochemical polymerization step.

The pH of the coating solution can be adjusted to a range of from about 2.5 to about 10 prior to the electrochemical polymerization step.

Prior to deposition of the polymeric coating, the conductive substrate can be cleaned in a number of ways with varying degrees of harshness, including but not limited to rinsing and/or ultrasonicating in water or soapy water, exposure to organic solvents such as acetone or alcohol, hydrogen peroxide, acids or etching solutions (e.g. Piranha etch), exposure to reactive plasma cleaning/etching such as $CF_4$, or microgrit blasting with media such as sodium bicarbonate, silica, and alumina.

After cleaning, the conductive substrate can be dried under a stream of nitrogen or argon to limit exposure to oxygen, which can contaminate the cleaned surface. Such cleaned substrates are stored (prior to coating) in oxygen-free environments (e.g., a glove box purged with nitrogen).

Methods herein can further include the step of roughening the conductive substrate prior to the electrochemical polymerization step. Roughening the conductive substrate can help to expose the preferred surface and/or to improve coating uniformity, conformality, and adhesion to the substrate. For example, the conductive substrate can be chemically roughened using an etching solution. Alternatively, the conductive substrate can be electrochemically roughened. Electrochemical roughening can include exposing the conductive substrate to voltage or current pulsing or cycling in a solution selected from the group consisting of hydrochloric acid, sulfuric acid, ethanolic saline, and a combination thereof. As a further alternative, the conductive substrate can be mechanically roughened. The mechanical roughening can be conducted by micro-grit blasting with media including but not limited to silica, alumina, and/or sodium bicarbonate.

The surface of the conductive substrate can be modified with an organic molecule layer. Non-limiting examples of an organic molecule layer include an oxide layer, a monolayer, a self-assembled monolayer, or a tie layer. Organic molecule surface modification can be employed to modulate physical properties of the coated substrate including but not limited to coating adhesion, conductivity, and uniformity. Non-limiting examples of surface functional groups include thiols and silanes. Molecular modification of the surface of the conductive substrate can be achieved in a number of ways, including but not limited to reactive plasma exposure, soaking/dip-coating or micro/nano spray with molecular solution, electrochemical mediated oxidation/reduction of a metal surface, and/or electro-grafting of molecular species.

A constant current or voltage can be used to drive the electrochemical polymerization reaction. The application of constant current or voltage typically results in a single layer polymer matrix, wherein the thickness of the layer is dependent upon the total amount of charge used to drive the electrochemical polymerization.

The current density used for deposition can range from about 0.1 $mA/cm^2$ to about 5 $mA/cm^2$ depending on various factors including the specific metals used. As a specific example, in the context of platinum, the current density can be about 0.1 $mA/cm^2$.

A potentiodynamic electrodeposition method can be used where voltage is swept or cycled from a low to high voltage. The application of cyclic voltage typically results in a coating with multiple interfaced layers of polymer matrix.

The electrochemical polymerization step is typically carried out inside a container or vessel containing at least 2 electrodes. In some embodiments, the container or vessel includes a working or sense electrode (WE); a counter or return electrode (CE) having approximately 10× the surface area of the WE, and which can be made of platinum, platinized titanium, or platinized niobium; and, optionally, a reference electrode (RE), which can be a KCl saturated $Ag/AgCl_2$ or calomel reference electrode.

The method can further include a step of applying actinic radiation. The actinic radiation can be sufficient to activate the photoactivatable groups associated with components of the coating. The actinic radiation can include UV light. For example, the wavelength of the UV light can be from about 260 to about 400 nm.

The present invention may be better understood with reference to the following examples. These examples are intended to be representative of specific embodiments of the invention, and are not intended as limiting the scope of the invention.

EXAMPLES

Example 1

Preparation of a Coating Solution (Polymerization Mixture) Comprising EDOT, an Anionic Photoreactive Cross-Linking Agent and an Anionic Photoreactive Hydrophilic Polymer A conducting polymer precursor solution (100 mL) was prepared comprising EDOT (0.090M) in a solution of 25% v/v isopropanol in water in a glass beaker. The beaker was placed on a magnetic stir plate, and a magnetic stir bar was used to stir the mixture at a speed fast enough to create a vortex in the center of the mixture, but not so fast that the mixture developed bubbles. While the mixture was being stirred, PLURONIC F68 10% solution (1 mL) was slowly added to stabilize the mixture.

After constant stirring at room temperature for approximately 12 hours, the aqueous EDOT mixture was fully transparent, with no visible globules of undissolved EDOT.

To this solution, 2.5 grams of a polyacrylamide-based photoreactive anionically-charged polymer (Photo-PA), 2.5 grams of a photoreactive polyvinylpyrrolidone (Photo-PVP), and 1 gram of an anionically-charged photoreactive crosslinker was added and left to stir for 4 hours.

The resulting polymerization mixture was white, and the conducting polymer monomer was in suspension.

Example 2

Preparation and Characterization of the Coated Electrode

A polymerization mixture was prepared using the procedure set forth in Example 1. A platinum electrode was selected as the conductive substrate. The platinum electrode surface was visually inspected for major defects, and was then cleaned and roughened by microgrit blasting (60 sec at distance of ~1.2 inch with 60-80 psi) with sodium bicarbonate or alumina using a VANIMAN SANDSTORM microabrasive sand blaster. The electrode substrate was then cleaned by ultrasonication in isopropanol and acetone.

The polymerization mixture was then transferred to a 3-electrode voltammetry cell connected to a BIO-LOGIC VMP3 potentiostat/galvanostat. The voltammetry cell contained the platinum electrode (conductive substrate) as the working electrode, a platinized niobium mesh (~10× larger surface area than the working electrode) as the counter electrode, and Ag/AgCl (saturated KCl) reference electrode. The voltammetry cell was filled with the conducting polymer precursor solution set forth in Example 1.

The electrodeposition reaction was initiated by driving the process at a constant current of 0.5 mA/cm$^2$ for a duration of 20 minutes onto the working electrode. The electrodeposition step was carried out at room temperature.

Upon removal from the voltammetry cell, the coated electrode appeared black, and the polymeric coating fully covered the portion of the conductive substrate that was submerged in the coating solution.

To initiate the crosslinking reaction of the photopolymers and crosslinkers, the coated electrode was transferred to the UV curing station and exposed to UV light at 350 nm for 5-10 minutes per side.

The BIO-LOGIC VMP3 potentiostat/galvanostat was used to perform the electrical characterization of the coated electrode.

Electrochemical impedance spectroscopy (EIS) was measured at frequencies from 1-100,000 Hz while applying 5 mV root mean square (RMS) sine wave between the working and counter electrode.

Cyclic voltammetry (CV) testing was performed to measure the charge storage and transfer properties of the electrodes. The current was measured as the voltage was cycled from +0.8 to −0.6 V versus the SCE at a rate of 0.1 V/s, starting at 0 V.

Additionally, it was determined that the coated electrode exhibited greater than a 50% improvement in impedance at frequencies below 1000 Hz and greater than a 100% increase in CSC (the amount of charge that can be stored and delivered over a given voltage and time range, as measured by cyclic voltammetry) as compared to the original, uncoated platinum electrode.

Extended stimulation of electrodes was performed with a NATIONAL INSTRUMENTS data acquisition system (cDAQ-9174) with the appropriate voltage and current cards running LAB VIEW software. A 2-electrode electrochemical cell with phosphate buffered saline (PBS, pH~7.0) was used as the electrolyte, the platinum conductive substrate as the working electrode, and a platinized niobium mesh as counter electrode. The system sourced 100-400 μs symmetric cathodic-first square waves with voltage magnitude of 1-3V which resulted in a pulse waveform with peak current density of 20 μC/cm$^2$ per phase at a rate of 1000 Hz. The extended stimulation was performed constantly for 100-120 hrs at room temperature. At the stimulation rate, this resulted in delivery of ~100 million pulses per 24 hour period.

The electrical durability of coated substrates were also tested using short-term cyclic voltammetry (CV) or current (I) pulsing-based stress tests. The objective of such short-term stress tests is that by increasing the cycling voltage or current amplitude in sequential rounds of acute electrical stress, the relative durability of the coating types can be discriminated in a short period of time (~1 hour).

Example 3

Abrasion Testing

The mechanical adhesion and abrasion resistance of the polymeric coating to the conductive substrate were evaluated using a custom-developed pull tester fixture with rubber O-rings that compress around coated rod-shaped substrates.

Example 4

Assessment of Lubricious Properties of Coatings

A portion equal to 15 cm of 18 cm long stainless steel hypotubes (3 mm diameter) were coated by electrodeposition within the following solutions:
Formulation 1 (solution of Example 1)
Formulation 2 (solution of Example 1 with the substitution of 0.5 g of a first anionically-charged photocrosslinker)
Formulation 3 (solution of Example 1 with the substitution of a second anionically-charged photocrosslinker different than the first at the same concentration)
Formulation 4 (solution of Example 1 without anionically-charged photocrosslinker)
Formulation 5 (solution of Example 1 with the substitution of 0.5 g of the second anionically-charged photocrosslinker)
PEDOT without hydrophilic polymers (prepared in accordance with U.S. Pat. App. No. 61/794,058 examples 1 and 4).

Lubricity was measured with a pinch force tester. Samples were hydrated in PBS for 60 s and pinched between 10 mm silicone pads with 500 grams force. The sample was then pulled normal to the pinch force at 1 cm/s and the drag force was measured. Samples were measured in triplicate.

Figure 3:
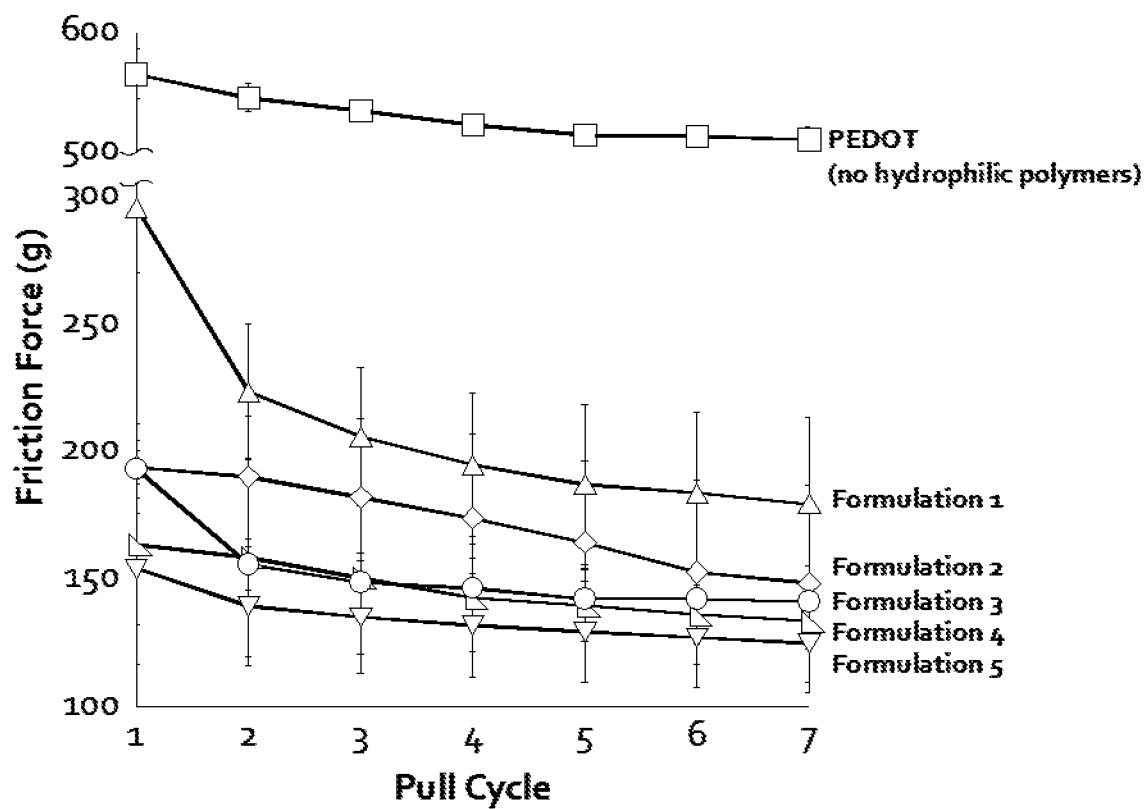
FIG. 3 is a graph showing measured friction force for various coatings over a number of pull cycles.

The results (FIG. 3) showed that the inclusion of hydrophilic polymers in the PEDOT coating greatly improved lubricity (i.e., decreased friction force). The friction force of the coatings prepared with hydrophilic polymers (variations of coatings produced by the solutions of Example 1) was 25-30% of the friction force of PEDOT coatings without hydrophilic polymers.

Example 5

UV Transmittance of Coatings

Although PEDOT-based combination conductive coatings appear very black and opaque by eye, the PEDOT component was found not to limit UV curing of the photoreactive components in the combination coatings. To test this, UV transmittance through coatings was measured. Glass slides (~7×17 mm) were coated with indium-tin oxide (ITO) to create a conductive surface. Coatings prepared by electrodeposition of solutions of Example 1 (Formulation A) or Example 1 without anionically charged photocrosslinker (Formulation B) were made on half of the ITO surface of each sample.

The transmission of white light was recorded with a camera-equipped microscope (no quantitation). The transmission of UV light was measured with a radiometer (International Light Technologies Model ILT1400) positioned 8 in. from the UV lamps (Heraeus Noblelight Model RQ436Z4). A plastic cap with a center hole of 5/32 in. was placed over the detector and samples were taped in place over this hole for measurement. This setup permitted measurement of only light passing through the conductive coating. The intensity of UV reaching the sensor was recorded 20 s after opening the UV shutter. Eight samples of each coating type were measured.

The coatings transmitted white light and exhibited blue-black to black colors. The coating that included the anionic photocrosslinker appeared more uniform than the coating without the anionic photocrosslinker.

The coatings permitted some UV light to pass through, but the amount of UV transmitted was a function of the coating composition. The percentage of UV light transmitted, relative to the ITO glass substrate, was 19±2% for formulation A and 41±3% for Formulation B.

The results of this simple measurement reveal that, despite expectations, UV light can penetrate PEDOT-based conductive coatings.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration to. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

The invention has been described with reference to various specific and preferred embodiments and techniques. However, it should be understood that many variations and modifications may be made while remaining within the spirit and scope of the invention.

The invention claimed is:

1. A coating solution for forming a conductive polymer layer consisting of:
   a conductive monomer, wherein the conductive monomer comprises 3,4-ethylenedioxythiophene (EDOT), a functionalized derivative of EDOT, or a mixture thereof;
   at least one photoreactive component comprising an anionic photoreactive hydrophilic polymer containing polyacrylamide and photoreactive groups;
   a non-charged hydrophilic polymer derived from 1-vinyl-2-pyrrolidone (PVP) comprising photoreactive functional groups;
   at least one solvent; and
   a surfactant.

2. The coating solution of claim 1, wherein the conductive monomer comprises the functionalized derivative of EDOT selected from the group consisting of hydroxymethyl-EDOT, EDOT-vinyl, EDOT-ether allyl, EDOT-COOH, EDOT-MeOH, EDOT-silane, EDOT-vinyl, EDOT-acrylate, EDOT-sulfonate, EDOT-amine, EDOT-amide, bi-EDOT, tri-EDOT, and combinations thereof.

3. The coating solution of claim 1, wherein a weight ratio of the anionic photoreactive hydrophilic polymer and the non-charged hydrophilic polymer is between about 1:10 and about 10:1.

4. The coating solution of claim 1, the at least one photoreactive component further comprising an anionic photoreactive cross-linking agent, the anionic photoreactive cross-linking agent comprising sulfonate, carboxylate, phosphonate, or phosphate groups, or combinations thereof.

5. The coating solution of claim 1, the at least one photoreactive component further comprising an anionic photoreactive cross-linking agent, and the anionic photoreactive cross-linking agent comprising disodium 4,5-bis[(4-benzoylbenzyl)oxy]-1,3-benzenedisulfonate or sodium bis (4-benzoylphenyl) phosphate; or the photoreactive component comprising the anionic photoreactive hydrophilic polymer, the anionic photoreactive hydrophilic polymer comprising poly[acrylamide-co-sodium-2-acrylamido-2-methylpropanesulfonate-co-N-(3-(4-benzoylbenzamido) propyl)methacrylamide] or N-acetylated poly[acrylamide-co-sodium-2-acrylamido-2-methylpropanesulfonate-co-N-(3-(4-benzoylbenzamido)propyl)methacrylamide]-co-methoxy poly(ethylene glycol).

6. The coating solution of claim 1, wherein the anionic photoreactive hydrophilic polymer further comprises sulfonate groups.

7. The coating solution of claim 1, the surfactant being selected from polaxamers, polyoxyethylene alkyl ethers, polysorbitan, or polyoxyethylene derivatives of sorbitan monolaurate.

8. The coating solution of claim 1, the at least one solvent comprising an aprotic organic solvent or a polar organic solvent.

9. The coating solution of claim 1, wherein the at least one solvent comprises at least one selected from the group consisting of acetonitrile, dichloromethane, dimethylsulfoxide, acetone, dimethylformamide, isopropanol, methanol, ethanol, water, and combinations thereof.

10. An electrically conductive coating comprising a reaction product of a polymerization mixture consisting of:
    a conductive monomer, wherein the conductive monomer comprises 3,4-ethylenedioxythiophene (EDOT), a functionalized derivative of EDOT, or a mixture thereof;
    at least one photoreactive component comprising an anionic photoreactive hydrophilic polymer containing polyacrylamide and photoreactive groups;
    a non-charged hydrophilic polymer derived from 1-vinyl-2-pyrrolidone (PVP) comprising photoreactive functional groups;
    at least one solvent and
    a surfactant.

11. A coated electrode comprising an electrode and the electrically conductive coating of claim 10, wherein the electrically conductive coating is disposed over at least a portion of the electrode.

* * * * *